United States Patent [19]

Bye

[11] 4,203,867
[45] May 20, 1980

[54] TRANSITION METAL COMPOSITION AND PRODUCTION THEREOF

[75] Inventor: Ashley D. Bye, Hague, Netherlands

[73] Assignee: Imperial Chemical Industries Limited, London, England

[21] Appl. No.: 936,892

[22] Filed: Aug. 25, 1978

[30] Foreign Application Priority Data

Aug. 31, 1977 [GB] United Kingdom ............... 36343/77
May 24, 1978 [GB] United Kingdom ............... 21733/78

[51] Int. Cl.$^2$ .............................................. C08F 4/64
[52] U.S. Cl. ............................... 252/429 B; 526/140; 526/141; 526/142
[58] Field of Search ..................................... 252/429 B

[56] References Cited

U.S. PATENT DOCUMENTS

| | | | |
|---|---|---|---|
| 3,094,568 | 6/1963 | Hay et al. | 252/429 B X |
| 3,149,097 | 9/1964 | Coover et al. | 252/429 B X |
| 3,178,401 | 4/1965 | Coover et al. | 252/429 B X |
| 3,210,332 | 10/1965 | Lyons et al. | 252/429 B X |
| 3,219,651 | 11/1965 | Hill et al. | 252/429 B X |
| 3,549,717 | 12/1970 | Itakura et al. | 252/429 B X |
| 3,652,705 | 3/1972 | Arakawa et al. | 252/429 B X |
| 3,660,519 | 5/1972 | Arakawa et al. | 252/429 B X |
| 3,960,765 | 6/1976 | Shiga et al. | 252/429 B |
| 3,984,350 | 10/1976 | Karayannis et al. | 252/429 B |
| 4,007,133 | 2/1977 | Rost et al. | 252/429 B |
| 4,115,532 | 9/1978 | Yamaguchi et al. | 252/429 B X |
| 4,115,533 | 9/1978 | Yamaguchi et al. | 252/429 B X |

FOREIGN PATENT DOCUMENTS

| | | |
|---|---|---|
| 2099150 | 2/1972 | France . |
| 2314924 | 1/1977 | France . |
| 2320308 | 3/1977 | France . |
| 1324173 | 7/1973 | United Kingdom . |
| 1336942 | 11/1973 | United Kingdom . |
| 1351822 | 5/1974 | United Kingdom . |
| 1359328 | 7/1974 | United Kingdom . |
| 1388308 | 3/1975 | United Kingdom . |
| 1391067 | 4/1975 | United Kingdom . |
| 1487393 | 9/1977 | United Kingdom . |

*Primary Examiner*—Patrick Garvin
*Attorney, Agent, or Firm*—Cushman, Darby & Cushman

[57] ABSTRACT

A transition metal composition has the formula:

$$TiCl_3(AlR_xX_{3-x})_n E_a L_b$$

where E is an ether or thioether; L is a defined ester, an amine or a ketone; and a and b are each greater than 0.001 and not more than 0.50. The composition has a low surface area, typically less than 50 m$^2$/g. The composition can be prepared by reacting titanium tetrachloride with an organo-aluminium compound, optionally heating the reaction product, contacting the reaction product at an elevated temperature with at least one of E and L and washing the product subsequent to the treatment with E. In the composition, E is conveniently di-n-butyl ether or di-isoamyl ether and L can be tetramethylethylenediamine; ethyl benzoate; benzophenone; glycerol monostearate; glycerol triacetate; glycerol tripalmitate; glycerol trimethacrylate; pentaerythritol tetra-acrylate or ethyl phenyl acetate. The composition can be used as a component of a catalyst for the polymerization of olefine monomers such as propylene. Copolymers having a useful combination of properties can be obtained.

15 Claims, No Drawings

TRANSITION METAL COMPOSITION AND PRODUCTION THEREOF

The present invention relates to transition metal compositions, the preparation of such compositions and the use of such compositions as a component of a catalyst system for the polymerisation of olefine monomers.

The polymerisation of olefine monomers using the so-called Ziegler-Natta catalysts has been known for a number of years. These catalysts comprise a compound of a transition metal together with an organic compound of a non-transition metal. There have been many proposals to improve the activity and/or stereospecificity of the catalyst system by the use of additional catalyst components or by modifying either the transition metal compound or the non-transition metal compound.

According to the present invention there is provided, as a new composition of matter, a product of the formula:

$$TiCl_3(AlR_xX_{3-n})_n E_a L_b$$

where
R is a hydrocarbyl group;
X is a halogen atom other than fluorine;
E is an ether or a thioether;
x is such that $0 \leq x \leq 3.0$;
n is from 0 up to 0.5;
a and b are each, independently, from 0.001 up to 0.50; and
L is an organic Lewis Base compound selected from esters of the formula $$R^1R^2R^3CCOOR^1;$$

esters and partial esters of aliphatic diols and polyols; amines of the formula $$R^4R^5R^6N;$$

and ketones of the formula $$R^7-\underset{\underset{O}{\|}}{C}-R^8$$

where
$R^1$ is a hydrocarbyl group;
$R^2$ and $R^3$ are each, independently, a hydrogen atom or a hydrocarbyl group; or the group $R^1R^2R^3C$— is a substituted or unsubstituted, saturated or unsaturated, condensed or uncondensed hydrocarbyl ring system;
$R^4$ and $R^5$ are hydrocarbyl groups;
$R^6$ is a hydrogen atom, a hydrocarbyl group or a group $$-C_mH_{2m}NR^4R^5;$$

or $R^4$ and $R^5$, optionally together with $R^6$, together form a substituted or unsubstituted, saturated or unsaturated, condensed or uncondensed ring system;
$R^7$ is a hydrocarbyl group;
$R^8$ is a hydrocarbyl group, which may optionally be substituted with one hydrocarbonoxy-group; and
m is 1, 2 or 3.

The group R is conveniently a hydrocarbyl group containing from 1 up to 20 carbon atoms and may be an alkyl, aryl, cycloalkyl, alkaryl or aralkyl group. Typically, the group R is an alkyl group containing from 2 up to 10 carbon atoms, for example an ethyl or butyl group.

Typically, X is chlorine and the value of x is such that $0 \leq x \leq 2.0$ and is especially about one.

The value of n is preferably greater than 0 and less than 0.3, especially greater than 0 and less than 0.2.

The ether or thioether which is E is a monoether, polyether, monothioether or polythioether which is capable of forming coordination complexes or compounds with aluminium halides or aluminium alkyls, these complexes or compounds being soluble in at least one of the solvents selected from the monoether, polyether, monothioether and polythioether themselves, aromatic and aliphatic hydrocarbons and the halogen-containing derivatives thereof.

The ether or thioether which is E is a compound containing only ether or only thioether groups. The polyether and the polythioether contain at least two ether groups or at least two thioether groups respectively. The ether or thioether may be a compound of the type $R^9-Z-R^{10}$ where $R^9$ and $R^{10}$, which may be the same or different, are hydrocarbyl groups containing 1 up to 12 carbon atoms; and Z is an oxygen or a sulphur atom.

The groups $R^9$ and $R^{10}$ are conveniently the same and may be alkyl, aryl, alkaryl, aralkyl or cycloalkyl groups. It is preferred that $R^9$ and $R^{10}$ are phenyl groups or particularly alkyl groups containing from 4 up to 6 carbon atoms. Polyethers which may be used as the compound E include 1-methoxy-2-(β-methoxyethoxy)ethane and 1,2-diphenoxyethane. It is especially preferred that E is di-n-butyl ether or di-isoamyl ether.

The compound L is an ester, ketone or amine, all of which are as hereinbefore defined. Organic Lewis Base compounds which may be used as the compound L and which are suitable for use as components of olefine polymerisation catalysts are disclosed, inter alia, in British Patent Specifications Nos. 809 717; 896 509; 920 118; 933 236; 1 017 977; 1 150 845; 1 208 815 and 1 324 173 and Belgian Patent Specification No. 693 551.

If the compound L is an ester of the formula $R^1R^2R^3CCOOR^1$ it may be ethyl benzoate or the ethyl ester of phenylacetic acid. Esters of aliphatic diols and polyols include glycerol monoacetate, glycerol monostearate, commercially available glycerol monostearate which may contain quantities of the di- and tri-stearates, glycerol triacetate, glycerol tripalmitate, glycerol trioleate, glycerol trimethacrylate and pentaerythritol tetra-acrylate. The amine may be a diamine such as N,N,N′,N′-tetramethylethlyenediamine. The ketone may be an aromatic ketone, such as benzophenone, or may be substituted with a hydrocarbonoxy group as in 4-methoxy-4-methyl-pentanone-2. The compound L is preferably an ester or an amine (as hereinbefore defined).

The values of a and b need not be the same and typically will be different. The value of a is conveniently from 0.01 up to 0.20 and the value of b is conveniently from 0.01 up to 0.20.

A particularly preferred composition of matter in accordance with the present invention has the formula $$TiCl_3(AlR^{11}_xCl_{3-x})_n(R^{12}_2O)_a L'_b$$

where
a, b, n and x are all as defined;

$R^{11}$ is an alkyl group having from 2 up to 10 carbon atoms;

$R^{12}$ is a phenyl group or an alkyl group having from 4 up to 6 carbon atoms; and L' is glycerol monostearate, glycerol monoacetate, glycerol tripalmitate, glycerol trimethacrylate, pentaerythritol tetra-acrylate, the ethyl ester of phenylacetic acid or N,N,N',N'-tetramethylethylenediamine.

The composition of matter has a relatively low specific surface area which is typically less than 50 m²/g and especially from 1 up to 30 m²/g. The term "specific surface area" as used herein is the surface area of one gramme of the product, the surface area having been measured using the technique of BS 4359/1.

The colour of the composition of matter may be from violet to brown and the composition of matter is typically reddish-brown in colour.

As a further aspect of the present invention there is provided a process for the production of a titanium trichloride-containing composition which process comprises (1) reducing titanium tetrachloride by reacting the titanium tetrachloride with a reducing agent under conditions to give a titanium trichloride product which includes an associated aluminium compound containing aluminium and chloride atoms, wherein the titanium trichloride is formed predominantly in the beta-form;

(2) contacting the reduction product with compound E and compound L either simultaneously or sequentially, at least part of the contacting being effected at a temperature of at least 60° C. in the presence of at least compound E or compound L; and (3) subsequent to the contacting with the compound E washing the product obtained with an inert hydrocarbon or inert halohydrocarbon liquid.

The reduction product may be subjected to a thermal treatment at a temperature in the range from 40° C. up to 130° C. for a period of from 5 minutes up to 20 hours, and the thermally treated product may then be subjected to stage (2) of the process.

After step (3), the product may be subjected to an additional treatment in which an aluminium alkyl compound, typically diethyl aluminium chloride, is added, followed by an olefine monomer, typically propylene, conveniently in an amount of 0.1 up to 2.0 grammes for each gramme of the titanium trichloride-containing product.

The various stages of the preparation of the titanium trichloride-containing product are preferably effected in the presence of a suitable inert hydrocarbon liquid which is stirred. This hydrocarbon liquid is conveniently an aliphatic or cycloaliphatic hydrocarbon such as hexane, heptane, decane or dodecane or mixtures thereof.

Suitable reducing agents include organic aluminium compounds of the general formulae

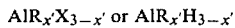
$AlR_{x'}X_{3-x'}$ or $AlR_{x'}H_{3-x'}$ wherein

R and X are both as hereinbefore defined and x' is such that $1.0 \leq x' \leq 3.0$; and it is preferred, when using such reducing agents, that the reduction is effected in the essential absence of aromatic hydrocarbons. An alternative reducing agent is a compound of the general formula

$TiCl_2 \cdot 2AlCl_3 \cdot arene$ where "arene" means a compound containing a six-membered hydrocarbon ring which ring contains a completely delocalised double bond system. The term "arene" includes benzene, toluene, xylene, durene and hexamethylbenzene and also compounds such as chlorobenzene. The compound $TiCl_2 \cdot 2AlCl_3 \cdot arene$ is soluble in aromatic liquids and thus reduction using this compound is effected either using a solution of the compound in an aromatic liquid or by grinding the solid compound in the presence of an excess of titanium tetrachloride.

If the reducing agent is an organic aluminium compound, it is conveniently one in which the value of x' is from 1.5 up to 2.0. However, satisfactory products may be obtained when x' has a value of 3.0. The organic aluminium compound may be aluminium triethyl or more preferably diethyl aluminium chloride or ethyl aluminium sesquichloride.

The reduction of the titanium tetrachloride is preferably carried out at a temperature which is below about 80° C. The temperature used depends on the particular reducing agent which is used. Thus, if the reducing agent is an alkyl aluminium sesquihalide, it is preferred to carry out the reduction at a temperature of between −20° C. and +20° C., very conveniently at 0° C. If the reducing agent is a dialkyl aluminium halide, whilst the temperature may be lower, for example as low as −40° C., satisfactory products can be obtained by using temperatures in the same range, that is temperatures in the range from −20° C. up to +20° C., although temperatures of −40° C. up to +10° C. are particularly suitable. If the reducing agent is an aluminium trialkyl, or an organic aluminium hydride, then lower reduction temperatures are preferred, particularly temperatures from −100° C. up to 0° C., especially about −70° C. up to about −40° C. If the reducing agent is an alkyl aluminium dihalide the preferred reduction temperatures are in the range from 0° C. up to 40° C., especially from 10° C. up to 30° C. Using the compound $TiCl_2 \cdot 2AlCl_3 \cdot arene$ as the reducing agent, the reduction may be effected at a temperature of from −80° C. up to +80° C., conveniently in the range from 0° C. up to 40° C.

The quantity of the reducing agent depends on the particular reducing agent which is used. Using an organic aluminium compound the proportion used is typically from 0.1 up to 2.0 moles of the organic aluminium compound for each mole of titanium tetrachloride. Using a dialkyl aluminium halide, or a material such as an aluminium sesquihalide which may be regarded as containing a proportion of a dialkyl aluminium halide, the preferred proportions of the organic aluminium compound are from 0.5 up to 1.5 moles of dialkyl aluminium halide for each mole of titanium tetrachloride. Using an aluminium trialkyl the preferred proportions are less and are typically in the range from 0.25 up to 0.5 mole for every mole of titanium tetrachloride. Using a compound of the type $TiCl_2 \cdot 2AlCl_3 \cdot arene$, it is preferred to use equimolar proportions of the two reactants or an excess quantity of titanium tetrachloride.

The titanium trichloride-containing product obtained in stage (1) of the process is a solid which may be separated from the reaction medium and washed several times and finally resuspended in a sample of fresh hydrocarbon liquid. However, it is preferred that stage (2) or the optional thermal treatment stage, is effected in the presence of the liquid reaction medium from stage (1) when the reducing agent is an organic aluminium compound.

In the optional thermal treatment stage, the reduction product is preferably heated to a temperature of at least 60° C. The time of heating is dependent on the temperature used and shorter times are preferably used at higher temperatures. It is preferred that the conditions of temperature and time are such that the heated product contains a small proportion of the layer lattice structure as shown by the X-ray diffraction pattern of this material.

If the optional thermal treatment stage is effected, it is preferred that the heated product is separated from the reaction medium and washed several times before effecting stage (2).

The compounds E and L may be added simultaneously or sequentially, and in the latter case the compounds E and L may be added in either order. It is preferred that the compound E and the compound L are added separately and useful results have been obtained when the compound E has been added first.

The contacting of the reduction product with the compounds E and L may be effected by adding one, or both, of the compounds to a stirred suspension of the reduction product at ambient temperature and then heating the mixture to the temperature of at least 60° C. However, it is preferred to heat the reduction product to the temperature of at least 60° C. and then add one, or both, of the compounds E and L to the heated material. Whilst it is not necessary to contact the reduction product at a temperature of at least 60° C. with both compound E and compound L, this procedure is preferred. Thus, it is especially preferred to heat the reduction product, which may have been subjected to the optional thermal treatment, to the temperature of at least 60° C., and, whilst maintaining that temperature, add first the compound E and thereafter the compound L. If desired, the contacting with either compound E or compound L may be repeated and using such a procedure the reaction product is preferably separated from the reaction mixture and washed before repeating the contacting with compound E or compound L.

Contacting with compounds E and L may be effected in more than one step, for example by repeating the contacting with at least one of the compounds E or L. Alternatively, a first contacting step may be effected with one of the compounds E and L and a further and separate contacting step is then effected with the other one of compounds E and L. If contacting is effected in more than one step, it may be sufficient to wash the product between the contacting steps and washing after the final contacting step may not be necessary. However, it will be appreciated that such a procedure is possible only if washing is effected after contacting with compound E and thereafter the final contacting step is effected without the addition of any of the compound E. A convenient technique for effecting such a procedure is to heat the product of stage (1) to the temperature of at least 60° C., add compound E to the heated product some time after the desired temperature has been attained, for example 30 minutes to two hours after attaining the desired temperature, wash the heated product, heat the washed product to the temperature of at least 60° C. and add compound L at any time after attaining the desired temperature.

If stage (2), the contacting with compounds E and L, is effected in a single step, then the final stage of the process is to wash the product of stage (2). However, it is not necessary to subject the titanium trichloride product to a final washing stage provided that the titanium trichloride product is not contacted with compound E after the final washing stage.

Although washing can be effected at various stages of the process, the only necessary washing stage is subsequent to the contacting, or the final contacting, with the compound E.

The amount of the compound E which is used is preferably from 0.5 up to 3.0 moles for every mole of titanium trichloride present in the reduction product and it is particularly preferred to use between 0.8 and 2.5 moles per mole of titanium trichloride present in the reduction product.

The amount of the compound L which is used is conveniently in the range from 0.01 up to 2.0 moles for each mole of titanium trichloride present in the reduction product. It is particularly preferred to use from 0.02 up to 0.5 mole of the compound L, especially from 0.04 up to 0.3 mole of the compound L.

It will be appreciated that the optimum proportions of the compounds L and E will be dependent on the particular compounds used, but these optimum proportions can be determined readily by experiment.

The temperature at which the contacting of the reduction product with the compound E and/or the compound L is effected is at least 60° C. and may be up to 150° C. It is preferred to use temperatures of at least 80° C. and not more than 130° C. Especially preferred temperatures are in the range from 90° C. up to 120° C. The heating time is preferably at least one hour and conveniently does not exceed 20 hours, preferably at least 2 hours and not more than 10 hours.

If compounds E and L are added to the reduction product at the temperature of at least 60° C., and the reduction product has been subjected to the optional thermal treatment stage, it is preferred that at least one of the compounds E or L is added as soon as the reduction product attains the desired temperature. If compounds E and L are added separately in a single step, the second of the two compounds is conveniently added 5 minutes to two hours, for example 30 minutes, after the addition of the first of the two compounds.

The new composition of matter in the present invention may be used as one component of an olefine polymerisation catalyst.

Thus, according to a further aspect of the present invention there is provided an olefine polymerisation catalyst comprising: (1) a titanium trichloride-containing material of the type hereinbefore described; and (2) at least one organo-metallic compound of aluminium, or of a non-transition metal of Group IIA of the Periodic Table, or a complex of an organo-metallic compound of a non-transition metal of Group IA or Group IIA of the Periodic Table with an organo-aluminium compound.

The organo-metallic component which is component (2) of the catalyst can be a Grignard reagent which is substantially ether-free or a compound such as diphenyl magnesium. Alternatively, this component can be a complex of an organo-metallic compound of a non-transition metal of Groups IA or IIA with an organo-aluminium compound, for example $Mg[Al(C_2H_5)_4]_2$ or lithium aluminium tetraalkyl. It is preferred that component (2) is an organo-aluminium compound such as a hydrocarbyl aluminium sulphate, a hydrocarbyl oxyhydrocarbyl aluminium, or particularly a trihydrocarbyl aluminium or dihydrocarbyl aluminium halide or hydride, especially triethylaluminium or diethylaluminium chloride since catalysts including triethylaluminium give a high polymerisation rate whilst catalysts including diethylaluminium chloride give a relatively high percentage yield of the desirable insoluble (isotactic) polymer. A mixture of compounds can be used if desired, for example, a mixture of a trialkyl aluminium and a dialkyl aluminium halide. It may be preferred to use catalysts giving a low level of residual halogen in the polymer product in which case the organo-metallic component is desirably a halogen-free compound, particularly a trihydrocarbyl aluminium.

The catalyst can also contain, in addition to components (1) and (2), a further component, component (3), which is an organo-Lewis Base compound. This can be any Lewis Base which is effective to alter the activity and/or stereospecificity of a Ziegler catalyst system. A wide range of Lewis Bases have such an effect and these include compounds containing phosphorus and/or nitrogen atoms, oxygen compounds such as ethers, esters, ketones, and alcohols, and their sulphur-containing analogues, silicon compounds such as silanes and siloxanes, sulphones, sulphonamides and fused-ring heterocyclic sulphur compounds. Catalysts containing organo-Lewis Base compounds, or complexes including organo-Lewis Base compounds, are disclosed, inter alia in British Patent Specifications Nos. 803 198; 809 717; 880 998; 896 509; 920 118; 921 954; 933 236; 940 125; 966 025; 969 074; 971 248; 1 013 363; 1 017 977; 1 049 723; 1 122 010; 1 150 845; 1 208 815; 1 234 657; 1 324 173; 1 359 328; 1 383 207; 1 423 658; 1 423 659 and 1 423 660; Belgian Patent Specification No. 693 551; and published German Patent Application No. 2 600 552. It is preferred to use, as the organo-Lewis Base compound, a Lewis Base which contains at least one atom of sulphur, nitrogen and/or phosphorus. Thus preferred organo-Lewis Base compounds, which can be used as the optional component (3) of the catalyst, include sulphur compounds such as diphenylsulphone, secondary or tertiary amines such as dibutylamine or tributylamine, diamines such as N,N,N',N'-tetramethylethylenediamine, and compounds which include both phosphorus and nitrogen atoms, such as hexamethylphosphoric triamide; N,N,N',N'-tetramethylethyl phosphorodiamidate; N,N,N',N',N''-pentamethyl-N''-$\beta$-dimethylaminoethylphosphoric triamide; 2-dimethylamino-1,3-dimethyl-1,3,2-diaza-phospholidine-2-oxide and octamethylpyrophosphoramide.

In addition to, or instead of, the organo-Lewis Base compound which is component (3), the catalyst may also include a substituted or unsubstituted polyene (component (4)), which may be an acyclic polyene such as 3-methylheptatriene(1,4,6) or a cyclic polyene such as cyclooctatriene, cyclooctatetraene or cycloheptatriene or derivatives of such cyclic polyenes such as the alkyl- or alkoxy-substituted cyclic polyenes; tropylium salts or complexes, tropolone or tropone.

The proportions of the various catalyst components can be varied widely depending both on the materials used and the absolute concentrations of the components. Typically for each gramme atom of the transition metal which is present in component (1) of the catalyst, there is present at least 0.05, and preferably at least 1.0, and if desired as many as 50 or even more, moles of component (2). In general it is preferred to use not more than 25 moles of the organo-metallic component for each mole of the transition metal catalyst compound present in component (1). If a Lewis Base is included, then for each mole of the transition metal compound there is conveniently present from 0.01 up to 10, preferably from 0.1 up to 4, moles of the Lewis Base, provided that the amount of Lewis Base is less than the amount of component (2). Any polyene which is present, plus any Lewis Base, should preferably, in total number of moles, be less than the number of moles of component (2). For each mole of component (2), the number of moles of polyene is conveniently in the range 0.01 up to 1.0, especially 0.05 up to 0.5, for example from 0.1 up to 0.2. If both Lewis Base and polyene are included, these can conveniently be used in equimolar proportions but the relative proportions of these components may be varied to give the optimum results.

The catalysts of the present invention are particularly suitable for the polymerisation and copolymerisation of olefine monomers by contacting at least one olefine monomer with a catalyst of the type hereinbefore defined.

More specifically, there is provided a process for the production of a polymer or copolymer of an olefine monomer wherein at least one olefine monomer, or a mixture of at least one olefine monomer and ethylene, is polymerised by contacting the at least one olefine, or mixture thereof with ethylene, under polymerisation conditions with an olefine polymerisation catalyst as hereinbefore defined.

Monomers which can be polymerised by the present process include butene-1, and 4-methylpentene-1 and particularly propylene. These olefines may be copolymerised together or preferably may be copolymerised with ethylene, conveniently using a sequential polymerisation process such as is described in British Pat. Nos. 970 478; 970 479 and 1 014 944.

Surprisingly, although component (1) of the catalyst system contains some titanium trichloride in the beta-form, it has been found that the process of the present invention can be used for the polymerisation of propylene to give a relatively low proportion of the undesirable soluble polymer. Furthermore, many of the catalyst systems give a high rate of polymerisation.

It is preferred to effect polymerisation using monomers (and diluents when used) which have a high degree of purity, for example a monomer containing less than 5 ppm by weight of water and less than 1 ppm by weight of oxygen. Materials having a high degree of purity can be obtained by processes such as those described in British Patent Specifications Nos. 1 111 493, 1 226 659 and 1 383 611.

Polymerisation can be carried out in the known manner, for example in the presence or absence of an inert diluent such as a suitably purified paraffinic hydrocarbon, in the liquid phase using excess liquid monomer or in the gaseous phase.

If polymerisation is effected in the gaseous phase, it may be effected by introducing the monomer, for example propylene, into the polymerisation vessel as a liquid and operating with conditions of temperature and pressure within the polymerisation vessel which are such that the liquid monomer vaporises, thereby giving an evaporative cooling effect, and essentially all of the polymerisation occurs with the monomer in the gaseous phase. Polymerisation in the gaseous phase is preferably effected using conditions which are such that the monomer is at a temperature and partial pressure which are close to the dew point temperature and pressure for that monomer. Such a procedure is described in more detail in published German Patent Application No. 2 616 356. Polymerisation in the gaseous phase can be effected using any technique suitable for effecting a gas solid reaction such as a fluidised bed reactor system, a stirred bed reactor system or a ribbon blender type of reactor.

Polymerisation may be effected either in a batch manner or on a continuous basis and the catalyst components may be introduced into the polymerisation vessel separately or all the catalyst components may be mixed together before being introduced into the polymerisation reactor.

The polymerisation can be effected in the presence of a chain transfer agent such as hydrogen or a zinc dialkyl, in order to control the molecular weight of the product formed. If hydrogen is used as the chain transfer agent, it is conveniently used in an amount of from 0.01 up to 5.0%, particularly from 0.05 up to 2.0% molar relative to the monomer. The amount of chain transfer agent will be dependent on the polymerisation conditions, especially the temperature, which is typically in the range from 20° C. up to 100° C., preferably from 50° C. up to 85° C.

Using catalysts in accordance with the present invention propylene may be polymerised to give a polymer having a high flexural modulus, for example at least 1.00 $GN/m^2$, particularly at least 1.30 $GN/m^2$ and especially up to 1.60 $GN/m^2$.

Polymers produced by the process of the present invention have a high molecular weight as indicated by the melt flow index measured according to ASTM Test Method D 1238-70, using Condition N (that is a temperature of 190° C. and a weight of 10 kgm). Polymers obtained in accordance with the present invention have a melt flow index of less than 200 and preferred polymers have a melt flow index of less than 100, particularly less than 50, for example between 5 and 50.

Various aspects of the present invention will now be described with reference to the following Examples which are illustrative of the invention. In the Examples, all operations were effected under an atmosphere of nitrogen unless otherwise indicated.

EXAMPLE 1

(A) Purification of n-heptane

A quantity of n-heptane supplied by British Drug Houses and conforming to the Institute of Petroleum specification was passed, at room temperature, through a column containing BTS catalyst and a molecular sieve. After this treatment, the only impurity which could be detected was toluene at a level of about 0.01% by volume. This will be referred to as "purified n-heptane".

A further quantity of n-heptane was purged with nitrogen at ambient temperature for one hour. This will be referred to as "purged n-heptane".

(B) Reduction of titanium tetrachloride

A solution of 4.21 moles of titanium tetrachloride in 2.2 liters of purified n-heptane was placed in a five-liter nitrogen-purged dry jacketed glass reaction vessel. The solution was cooled to a temperature in the range 8° C. to 10° C. and stirred at 250 rpm. A solution of ethyl aluminum sesquichloride in n-heptane (containing 500 grammes of the sesquichloride for each liter of n-heptane) was added to the contents of the reaction vessel over a period of 90 minutes. The quantity added was sufficient to provide 2.868 moles of the ethyl aluminium sesquichloride (this contained 2.868 moles of diethyl aluminium chloride). The temperature was maintained at 8° C. to 10° C. throughout the addition and the mixture was stirred. At the end of the addition of the sesquichloride solution, the mixture was stirred for a further 4 hours whilst maintaining the temperature of 8° C. to 10° C.

The whole mixture was then heated up to a temperature of 90° C. whilst still stirring. The temperature was maintained at 90° C. for 90 minutes, the mixture was allowed to cool and settle, the supernatant liquid was decanted off and the residual solid was then washed 5 times using 2 liters of purified n-heptane for each wash. The washed product was then suspended in 2.5 liters of purified heptane and the suspension obtained was then split up into several portions which were treated in the following manner.

(C) Treatment with di-n-butyl ether

A portion equivalent to one-sixth of the suspension obtained by the foregoing procedure was then treated with neat di-n-butyl ether in the following manner. The suspension was heated to 90° C. and when the temperature of 90° C. had been attained 1.1 mole of di-n-butyl ether was added for each mole of titanium trichloride present in the suspension, which was being stirred. The temperature of 90° C. was maintained for one hour whilst continuing to stir the mixture.

(D) Treatment with glycerol monostearate

After the mixture had been at 90° C. for one hour, glycerol monostearate was added, as a solid, in a sufficient quantity to provide 0.05 mole of glycerol monostearate for each mole of titanium trichloride present. The glycerol monostearate used was a commercially available material, available under the trade name 'Atmos' 150, and believed to contain minor quantities of glycerol di- and tri-stearate. Heating at 90° C. was continued for one hour with stirring. The mixture was then allowed to cool to room temperature and the solid was allowed to settle. The supernatant liquid was decanted off and the solid was then washed twice with purified n-heptane and then three times with purged n-heptane using 500 ml of n-heptane for each wash. A sample of the product was dried and subjected to analysis. The remainder of the product was suspended in 500 ml of purged n-heptane.

EXAMPLE 2

The procedure described in respect of Example 1 was repeated with the exception that the glycerol monostearate was replaced by N,N,N',N'-tetramethylethylenediamine which was used in an amount of 0.30 mole of the diamine for each mole of titanium trichloride present in the product.

During the preparation the suspension could be handled easily and there were no problems of agglomeration. The product had a good particle form and could be handled readily.

EXAMPLES 3 TO 5

The procedure described in respect of Example 1 was repeated with the exception that the glycerol monostearate was replaced by varying proportions of the ethyl ester of phenylacetic acid. The quantities of the ester used are set out in Table 1.

Table 1

| Example No. | Mole EPA per mole $TiCl_3$ (a) |
|---|---|
| 3 | 0.05 |
| 4 | 0.10 |

Table 1-continued

| Example No. | Mole EPA per mole TiCl₃ (a) |
|---|---|
| 5 | 0.30 |

Note to Table 1
(a) EPA means ethyl ester of phenylacetic acid.

EXAMPLE 6

The procedure of Example 1 was repeated except that the glycerol monostearate was replaced by 0.15 mole of ethyl benzoate. Additionally, subsequent to the heating of the reduction product, all the washing and heating steps were effected in a mixed aliphatic hydrocarbon consisting predominantly of $C_{12}$ isomers.

COMPARATIVE EXAMPLE A

Treatment with di-n-butyl ether only

The reduced and heat-treated solid used in the preparation of the product of Example 6 was heated to 90° C. and 1.1 mole of di-n-butyl ether was added for each mole of titanium trichloride. The temperature was maintained at 90° C. for two hours and the product obtained was washed 5 times. Subsequent to the heating of the reduction product, all stages were effected using the same aliphatic hydrocarbon as was used in Example 6.

EXAMPLES 7 TO 10

The procedure of Example 1 was repeated with the exception that the glycerol monostearate was replaced by 0.15 mole of a different ester or a ketone. Further details are given in Table 2.

Table 2

| Example No. | Ester or ketone used (b) |
|---|---|
| 7 | GTA |
| 8 | GMA |
| 9 | BP |
| 10 | MMP |

Notes to Table 2
(b) GTA is glycerol triacetate
GMA is glycerol monoacetate
BP is benzophenone
MMP is 4-methoxy-4-methyl-pentanone-2.

The products of Examples 1 and 2 were subjected to chemical analysis and the surface area of the product of Example 2 was determined.

The results are set out in Table 3.

Table 3

| Product of Example | Al:Ti (atomic ratio) | Cl:Ti (atomic ratio) | Surface Area (m²/g) |
|---|---|---|---|
| 1 | 0.149 | 3.44 | |
| 2 | 0.157 | 3.42 | 10.6 |

EXAMPLES 11 TO 20

Polymerisations were carried out in a 20 gallon (91 liter) stainless steel autoclave.

64 liters of the same hydrocarbon diluent as was used in the latter part of the process of Example 6, were charged into the vessel, and degassed at 60° C. for 30 minutes at a pressure of 50 millimeters of mercury. Propylene containing 0.15% by volume of hydrogen, was then admitted to the vessel in an amount to give a pressure of 1 psi (6.9 kN/m²) gauge. The diluent was stirred and stirring was continued throughout the following procedures. 0.536 mole of diethyl aluminium chloride, as a 25% by weight solution in the hydrocarbon diluent, was then added to the autoclave followed by 1 liter of the hydrocarbon diluent. 0.134 mole of titanium trichloride (prepared as described in Examples 1 to 10 or Comparative Example A) was added as a suspension of titanium trichloride in the hydrocarbon diluent. 2 liters of the hydrocarbon diluent were then added.

The autoclave was maintained at 60° C. while propylene was passed into the autoclave at a constant rate of 22 pounds per hour (about 10 kilograms per hour). The propylene charge contained 0.15% by volume of hydrogen. A total of 33.5 kilograms of propylene were passed into the autoclave, after which the propylene feed was terminated and the autoclave pressure was allowed to run down to 5 psi (34.5 kN/m²) gauge. The residual propylene was then vented off and the polymer suspension passed into a glass-lined vessel. The autoclave was washed with 20 liters of the diluent which was also added to the glass-lined vessel. The contents of the glass-lined vessel were mixed with isopropanol in an amount of 2% by volume relative to the diluent. The mixture was stirred for one hour at 70° C., a mixture of isopropanol and water (containing 10% by volume of water) was added in an amount of 0.6% by volume relative to the diluent and stirring at 70° C. was continued for a further 2 hours.

The polymer suspension was then run into a further vessel containing 40 liters of demineralised water at ambient temperature, and the mixture was stirred for 30 minutes. The aqueous phase was then decanted off and a further 40 liters of demineralised water at ambient temperature were added and the process was repeated. The diluent was then filtered off and the polymer was dried at 100° C. in the fluidised bed using nitrogen as fluidising gas.

The results obtained, which include information on the properties of the polymer formed, are set out in Table 4.

Table 4

| Ex or Comp Ex (c) | Form of TiCl₃ (d) | Yield of soluble polymer (% by wt) Dil (e) | Yield of soluble polymer (% by wt) Res (f) | P.D. (g/l) (g) | MFI (h) | F.M. (GN/m²) (i) | Act (j) |
|---|---|---|---|---|---|---|---|
| 11 | 1 | 2.6* | | | | | |
|    |   | 3.4 | 4.3 | 408 | 20 | 1.46 | 24.6 |
| 12 | 2 | 1.8* | | | | | |
|    |   | 1.9 | 2.2 | 488 | 10 | 1.54 | 9.1 |
| 13 | 3 | 3.0* | | | | | |
|    |   | 4.2 | 1.6 | 510 | 21.5 | 1.42 | 22.9 |
| 14 | 4 | 3.9* | | | | | |
|    |   | 4.7 | 4.2 | 513 | 15 | 1.40 | 14.4 |
| 15 | 5 | 1.3* | | | | | |
|    |   | 1.3 | 3.7 | 513 | 4 | 1.50 | 2.0 |
| 16 | 6 | 4.6* | | | | | |
|    |   | 5.3 | 4.0 | 525 | 9 | 1.41 | 16.3 |
| B  | A | 5.2* | | | | | |
|    |   | 6.9 | 3.9 | 494 | 17 | 1.33 | 20.4 |
| 17 | 7 | 5.7* | | | | | |
|    |   | 6.3 | 4.5 | 488 | 15 | 1.42 | 10.3 |
| 18† | 8 | 4.9* | | | | | |
|    |   | 5.8 | 4.8 | 500 | 28.5 | 1.52 | 18.6 |
| 19 | 9 | 6.5* | | | | | |
|    |   | 6.8 | 2.8 | 494 | 9.5 | 1.46 | 9.5 |

Table 4-continued

| Ex or Comp Ex (c) | Form of TiCl₃ (d) | Yield of soluble polymer (% by wt) Dil (e) | Res (f) | P.D. (g/l) (g) | MFI (h) | F.M. (GN/m²) (i) | Act (j) |
|---|---|---|---|---|---|---|---|
| 20 | 10 | 4.6* | | | | | |
| | | 4.6 | 2.7 | 482 | 9 | 1.44 | 8.6 |

Notes to Table 4
(c) + in these polymerisations, the quantities of diethyl aluminium chloride and titanium trichloride used were 0.536 mole and 0.268 mole respectively.
(d) Product of Examples 1 to 10, or Comparative Example A respectively.
(e) Polymer dissolved in the polymerisation diluent-determined by taking an aliquot portion of the polymerisation diluent at the end of the polymerisation after adding the isopropanol.
*determined by taking an aliquot portion of the polymerisation diluent at the end of the polymerisation before adding the isopropanol.
(f) The residual soluble polymer - determined by dissolving 1 gramme of solid polymer in 50 ml of the hydrocarbon diluent by heating at 185° C. The solution is cooled to 60° C. and stirred at this temperature for 18 hours. The precipitated polymer is separated by filtration at 60° C., and the proportion of polymer which remains dissolved in the diluent at 60° C. is determined by heating the solution to dryness.
(g) Packing density (P.D.) - determined by introducing 10 grammes of the polymer powder into a 50 ml flat-bottomed graduated tube of 2 cm internal diameter. The powder was compacted by striking the base of the tube against a horizontal surface a total of 30 times. The volume occupied by the polymer powder was then determined. Duplicate measurements were made.
(h) The melt flow index (MFI) was measured by ASTM Test Method D 1238-70, Condition N (190° C. and 10 kg).
(i) The flexural modulus (F.M.) was measured using a cantilever beam apparatus as described in Polymer Age, March 1970, pages 57 and 58. The deformation of a test strip at 1% skin strain after 60 seconds at 23° C. and 50% relative humidity was measured. The test strip, which had dimensions of approximately 150 × 19 × 1.6 mm, was prepared by mixing 23 g of the polymer with 0.1% by weight of an anti-oxidant ('Topanol' CA), and adding the mixture to a Brabender Plasticiser, at 190° C. 30 rpm and under a load of 10 kg to convert it to a crepe. The crepe was placed within a template, between aluminium foil and pressed by means of an electric Tangye press at a temperature of 250° C. The pressing was pre-heated for a period of 6 minutes, under just enough pressure to make the polymer flow across the template, that is an applied force of about 1 tonne. After the pre-heat period, the applied force was raised to 15.24 tonnes in 5.08 tonne increments, degassing (that is releasing pressure) every 5.08 tonnes. After 2 minutes at 15.24 tonnes, the press was cooled by means of air and water for 10 minutes or until room temperature was reached. The plaque obtained was then cut into strips of dimensions 150 × 19 × 1.6 mm. Duplicate strips of each polymer were placed into an annealing oven at 130° C. and after 2 hours at this temperature the heat was switched off and the oven cooled to ambient temperature at 15° C. per hour.
(j) Activity (Act) is calculated from the weight of monomer fed per millimole of TiCl₃ in the catalyst during the final hour of the polymerisation for each atmosphere pressure of propylene. The propylene pressure is determined by correcting the total pressure for the presence of inert materials such as nitrogen and propane which are determined by titrating the gas space at the end of the polymerisation with bromine water.

EXAMPLES 21 TO 25

The procedure of Example 1 was repeated except that the n-heptane diluent was replaced at all stages by a hydrocarbon fraction consisting mainly of $C_7$ isomers and having a boiling point range of 97° C. to 103° C. and the glycerol monostearate was replaced by 0.05 mole, for each mole of titanium trichloride, of a different ester. Further details are given in Table 5.

Table 5

| Example No. | Ester used (k) |
|---|---|
| 21 | GTP |
| 22 | GTB |
| 23 | GTO |
| 24 | GTM |
| 25 | PETA |

Notes to Table 5
(k) GTP is glycerol tripalmitate
GTB is glycerol tributyrate
GTO is glycerol trioleate
GTM is glycerol trimethacrylate
PETA is pentaerythritol tetra-acrylate.

EXAMPLE 26

A solution of 4.0 moles of titanium tetrachloride in 880 ml of the same hydrocarbon diluent as was used in the latter part of the process of Example 6, was placed in a 6.5 liter nitrogen-purged dry jacketed glass reaction vessel. The solution was maintained at a temperature of 25° C. and stirred at 250 rpm. A solution of ethyl aluminium sesquichloride in the hydrocarbon diluent (containing 0.85 mole of diethyl aluminium chloride for each liter of the solution) was added to the contents of the reaction vessel over a period of 4 hours. The quantity added was sufficient to provide 2.0 moles of the ethyl aluminium sesquichloride (this contained 2.0 moles of diethyl aluminium chloride). The temperature was maintained at 25° C. throughout the addition and the mixture was stirred. At the end of the addition of the sesquichloride solution, the mixture was stirred for a further one hour whilst maintaining the temperature of 25° C.

The whole mixture was then heated up to a temperature of 90° C. whilst still stirring. The temperature was maintained at 90° C. for 90 minutes, the mixture was allowed to cool and settle, the supernatant liquid was decanted off and the residual solid was then washed 5 times using 3 liters of the hydrocarbon diluent for each wash. The washed product was then suspended in 3 liters of the hydrocarbon diluent and the suspension obtained was then split up into several portions.

One portion was treated as described in Example 1 with the exception that the n-heptane diluent was replaced, at all stages, by the hydrocarbon diluent and the glycerol monostearate was replaced by 0.10 mole, for each mole of titanium trichloride, of the ethyl ester of phenylacetic acid.

EXAMPLES 27 AND 28

The procedure of Example 1 was repeated with a number of variations as follows:

All stages of the procedure were carried out using the same hydrocarbon diluent as was used in the latter part of the process of Example 6.

Reduction was effected by using the solution of ethyl aluminium sesquichloride in an amount sufficient to provide 0.7 mole of diethyl aluminium chloride for each mole of titanium tetrachloride.

The reduced product was initially heated at 110° C.

The treatment with di-n-butyl ether and the ester was effected at different temperatures, using a different ester in different proportions as set out in Table 6.

Table 6

| Example No. | Temperature of contacting with ether and ester (°C.) | Ester used Type (a) | Amount (mole/mole TiCl₃) |
|---|---|---|---|
| 27 | 110 | EPA | 0.15 |
| 28 | 115 | EPA | 0.10 |

Note to Table 6
(a) is as defined in Notes to Table 1.

EXAMPLES 29 to 34

The products of Examples 21 to 26 were used to polymerise propylene using the procedure of Examples 11 to 20. The results obtained are set out in Table 7.

Table 7

| Ex (c) | Form of TiCl$_3$ (1) | Yield of soluble polymer (% by wt) Dil (e) | Res (f) | P.D. (g/l) (g) | F.M. MFI (h) | (GN/m$^2$) (i) | Act (j) |
|---|---|---|---|---|---|---|---|
| 29 | 21 | 6.84 | 3.77 | 500 | 12.0 | 1.46 | 18.4 |
| 30 | 22 | 6.61 | 3.39 | 500 | 10.4 | 1.41 | 3.4 |
| 31 | 23 | 12.18 | 4.39 | 506 | 8.3 | 1.34 | 10.0 |
| 32 | 24 | 5.27 | 4.02 | 482 | 21.5 | 1.43 | 21.6 |
| 33 | 25 | 5.70 | 4.51 | 500 | 26.4 | 1.40 | 24.2 |
| 34† | 26 | 2.89 | 2.07 | 381 | 8.7 | 1.59 | 7. |

Notes to Table 7
Notes (c) and (e) to (j) are as defined in Notes to Table 4.
(1) Product of Examples 21 to 26.

EXAMPLES 35 AND 36

The titanium trichloride products of Examples 27 and 28 were used to prepare a copolymer of propylene with ethylene.

Polymerisation was effected in a 20 gallon (91 liter) stainless steel autoclave. 64 liters of the hydrocarbon diluent (as used in Examples 11 to 20) were charged into the vessel and degassed at 60° C. for 30 minutes at a pressure of 50 mm Hg. Propylene containing 0.175% by volume of hydrogen was then admitted to the vessel at a rate of 22 lbs/hr in an amount to give a pressure of 1 psi (6.9 kN/m$^2$) gauge. A vent on the vessel was opened and the propylene/hydrogen addition was continued for a further 5 minutes, the pressure in the autoclave being maintained at 1 psi gauge throughout. The vent was then closed and the addition of the propylene/hydrogen mixture stopped. The contents of the vessel were stirred throughout the following procedures. 0.536 mole of diethyl aluminium chloride, as a 25% by weight solution in the hydrocarbon diluent, was added to the autoclave, followed by 1 liter of the hydrocarbon diluent. 0.268 mole of the titanium trichloride product of Example 27 or Example 28 was added as a suspension of the titanium trichloride in the hydrocarbon diluent. This was washed in with a further 1 liter of hydrocarbon diluent.

The autoclave temperature was maintained at 60° C. whilst a total of 60.3 lbs (27.4 kg) of propylene containing 0.175 volume % of hydrogen was passed into the autoclave at a constant rate of 22 lbs/hour (about 10 kg/hour), after which the propylene/hydrogen feed was terminated and the autoclave pressure was allowed to run down to 10 psi (69 kN/m$^2$) gauge, (equivalent to 20 psi (138 kN/m$^2$) absolute) of propylene, the excess pressure being due to the presence of inert materials. A total of 2.07 kg of ethylene was then metered into the autoclave at a feed rate of 2.3 kg/hour for 20 minutes, then 4.0 kgm/hour for 20 minutes. The ethylene feed was then terminated and the autoclave pressure allowed to run down to a total pressure of 2 psi (13.8 kN/m$^2$) gauge.

The polymer suspension was passed into a 20 gallon (91 liter) glass-lined vessel. The autoclave was washed with 20 liters of the hydrocarbon diluent which was also added to the glass-lined vessel. The contents of the glass-lined vessel were mixed with isopropanol in an amount of 3% by volume relative to the diluent. The mixture was stirred for ½ hour at 70° C., and a mixture of isopropanol and distilled water (containing 10% by volume of water) was added in an amount of 0.6% by volume relative to the diluent and stirring at 70° C. continued for a further 1½ hours.

The polymer suspension was run into a further 20 gallon vessel containing 40 liters of demineralised water at ambient temperature and the mixture was stirred for 30 minutes. The stirrer was then stopped and the aqueous phase decanted off. A further 40 liters of demineralised water were added, stirring restarted and the process repeated. The diluent was then filtered off and the polymer was dried at 100° C. in a fluidised bed using nitrogen as the fluidising gas.

Further details of the process used and the properties of the polymers obtained are set out in Table 8.

Table 8

| Ex | Form of TiCl$_3$ (m) | C$_2$ (wt %) (n) | Yield of Soluble Polymer (% by wt) Dil (e) | Res (f) | P.D. (g/l) (g) | MFI (h) | F.M. (GN/m$^2$) (i) | LTBP (°C.) (o) | Act (j) |
|---|---|---|---|---|---|---|---|---|---|
| 35 | 27 | 5.1 | 5.40 | 8.68 | 522 | 19.0 | 1.31 | −25 | 4.5 |
| 36 | 28 | 5.3 | 5.37 | 6.51 | 503 | 37.0 | 1.31 | −19 | 8.2 |

Notes to Table 8
Notes (e) to (j) are as defined in Notes to Table 4.
(m) Product of Example 27 or Example 28.
(n) C$_2$ is the ethylene content of the polymer.
(o) The low temperature brittle point (LTBP) was determined using the technique of ASTM Test Method D 746 modified by using specimens and specimen holder as in ASTM Bulletin No. 231, July 1958. The specimens were cut from a plaque prepared in the same manner as that from which were cut the test strips used in the flexural modulus test (Note (i) to Table 4).

EXAMPLES 37 AND 38

The procedure of Examples 35 and 36 was repeated except that a total of 55.3 lbs (25.1 kg) of propylene containing 0.145% by volume of hydrogen was added to the autoclave, after which the feed was terminated and the autoclave pressure allowed to run down to 18 psi (124 kN/m$^2$) gauge (equivalent to 30 psi (207 kN/m$^2$) absolute of propylene). A total of 4.4 kg of ethylene was then added at a feed rate of 2.3 kg/hour for 20 minutes and then 4.0 kg/hour for 56 minutes. Ethylene feed was terminated and the autoclave pressure allowed to run down to 2 psi (13.8 kN/m$^2$) gauge. The polymer suspension was then treated as described in Examples 35 and 36.

Further details of the process used and the properties of the polymers obtained are set out in Table 9.

Table 9

| Ex | Form of TiCl₃ (m) | C₂ (wt %) (n) | Yield of Soluble Polymer (% by wt) Dil (e) | Res (f) | P.D. (g/l) (g) | MFI (h) | F.M. (GN/m²) (i) | LTBP (°C.) (o) | Act (j) |
|---|---|---|---|---|---|---|---|---|---|
| 37 | 27 | 11.8 | 7.23 | 11.86 | 457 | 5.9 | 1.08 | −43 | 5.5 |
| 38 | 28 | 12.5 | 4.53 | 10.17 | 488 | 3.4 | 1.08 | −43 | 8.0 |

Notes to Table 9
Notes (e) to (j) are as defined in Notes to Table 4.
Notes (m) to (o) are as defined in Notes to Table 8.

I claim:

1. A composition of matter which is of the formula:

$$TiCl_3(AlR_xX_{3-x})_nE_aL_b$$

where
R is a hydrocarbyl group;
X is a halogen atom other than fluorine;
E is a hydrocarbyl ether or a hydrocarbyl thioether;
x is such that $0<x<3.0$;
n is from 0 up to 0.5;
a and b are each, independently, from 0.001 up to 0.50; and
L is an organic Lewis Base compound selected from esters of the formula $$R^1R^2R^3CCOOR^1;$$

hydrocarbyl esters and partial esters of aliphatic hydrocarbyl diols and hydrocarbyl polyols; amines of the formula $$R^4R^5R^6N;$$

and ketones of the formula $$R^7-\underset{\underset{O}{\|}}{C}-R^8$$

where
R¹ is a hydrocarbyl group;
R² and R³ are each, independently, a hydrogen atom or a hydrocarbyl group; or the group R¹R²R³C— is an unsubstituted or hydrocarbyl substituted, saturated or unsaturated, condensed or uncondensed hydrocarbyl ring system;
R⁴ and R⁵ are hydrocarbyl groups;
R⁶ is a hydrogen atom, a hydrocarbyl group or a group $$-C_mH_{2m}NR^4R^5;$$

or R⁴ and R⁵, optionally together with R⁶, together form an unsubstituted, condensed or uncondensed hydrocarbyl ring system;
R⁷ is a hydrocarbyl group;
R⁸ is a hydrocarbyl group, which may optionally be substituted with one hydrocarbonoxy-group; and
m is 1, 2 or 3.

2. The composition of claim 1 wherein the group R is an alkyl group containing from 2 up to 10 carbon atoms, X is chlorine and the value of x is such that $0 \leq x \leq 2.0$.

3. The composition of claim 1 wherein E is di-n-butyl ether or di-isoamyl ether.

4. The composition of claim 1 wherein the compound L is the ethyl ester of phenylacetic acid, glycerol monoacetate, glycerol monostearate, glycerol tripalmitate, glycerol trimethacrylate, pentaerythritol tetra-acrylate or N,N,N',N'-tetramethylethylenediamine.

5. The composition of claim 1 wherein the values of a and b are different and the value of each is from 0.01 up to 0.20.

6. The composition of claim 1 wherein the specific surface area is from 1 up to 30 m²/g.

7. A composition as claimed in claim 1 whereof the colour is reddish-brown.

8. A process for the production of a titanium trichloride-containing composition which process comprises
(1) reducing titanium tetrachloride by reacting the titanium tetrachloride with a reducing agent under conditions to give a titanium trichloride product which includes an associated aluminium compound containing aluminium and chloride atoms, wherein the titanium trichloride is formed predominantly in the beta-form;
(2) contacting the reduction product with compound E and compound L either simultaneously or sequentially, at least part of the contacting being effected at a temperature of at least 60° C. in the presence of at least compound E or compound L; and
(3) subsequent to the contacting with the compound E washing the product obtained with an inert hydrocarbon or inert halohydrocarbon liquid
wherein
E is a hydrocarbyl ether or a hydrocarbyl thioether; and
L is an organic Lewis Base compound selected from esters of the formula $$R^1R^2R^3CCOOR^1;$$

hydrocarbyl esters and partial esters of aliphatic hydrocarbyl diols and hydrocarbyl polyols; amines of the formula $$R^4R^5R^6N;$$

and ketones of the formula $$R^7-\underset{\underset{O}{\|}}{C}-R^8$$

where
R¹ is a hydrocarbyl group;
R² and R³ are each, independently, a hydrogen atom or a hydrocarbyl group; or the group R¹R²R³C— is an unsubstituted or hydrocarbyl substituted, saturated or unsaturated, condensed or uncondensed hydrocarbyl ring system;

$R^4$ and $R^5$ are hydrocarbyl groups;

$R^6$ is a hydrogen atom, a hydrocarbyl group or a group $$-C_mH_{2m}NR^4R^5;$$

or $R^4$ and $R^5$, optionally together with $R^6$, together form an unsubstituted or hydrocarbyl substituted, saturated or unsaturated, condensed or uncondensed hydrcarbyl ring system;

$R^7$ is a hydrocarbyl group;

$R^8$ is a hydrocarbyl group, which may optionally be substituted with one hydrocarbonoxy-group; and $m$ is 1, 2 or 3.

9. The process of claim 8 wherein the product of stage (1) is subjected to a thermal treatment at a temperature in the range from 40° C. up to 130° C. for a period of from 5 minutes up to 20 hours, and the thermally treated product is then subjected to stage (2) of the process.

10. The process of claim 8 wherein the reducing agent is an organic aluminium compound of the formula

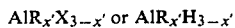

and the reduction is effected in the essential absence of aromatic hydrocarbons, wherein R is a hydrocarbyl group;

X is a halogen atom other than fluorine; and $x'$ is such that $1.0 \leq x' \leq 3.0$.

11. The process of claim 8 wherein, in stage (2), the compound E and the compound L are added separately, the compound E is added first, and is added as soon as the reduction product attains the desired temperature of at least 60° C.

12. The process of claim 8 wherein, in stage (2), the reduction product is heated to a temperature in the range from 90° C. up to 120° C., and the heating time is at least 2 hours and not more than 10 hours.

13. The process of claim 8 wherein, the stage (2), the reduction product is contacted with compound E at the temperature of at least 60° C., the product is washed and the washed product is contacted with compound L at the temperature of at least 60° C.

14. In an olefine polymerisation catalyst comprising: (1) a titanium trichloride-containing material; and (2) at least one organo-metallic compound of aluminium, or of a non-transition metal of Group IIA of the Periodic Table, or a complex of an organo-metallic compound of a non-transition metal of Group IA or Group IIA of the Periodic Table with an organo-aluminium compound, the improvement which comprises using as the titanium trichloride-containing material, the composition of matter of claim 1.

15. The compositions of claim 1, wherein said esters of aliphatic diols and polyols are selected from the group consisting of glycerol monoacetate, glycerol monostearate, commercially available glycerol monostearate which may contain quantities of the di- and tri-stearates, glycerol triacetate, glycerol tripalmitate, glycerol trioleate, glycerol trimethacrylate and pentaerythritol tetra-acrylate.

* * * * *